United States Patent [19]
Ohtsuki et al.

[11] Patent Number: 5,648,507
[45] Date of Patent: Jul. 15, 1997

[54] 14α-HYDROXY-4-ANDROSTENE-3,6,17-TRIONE HYDRATE AND PROCESS FOR PRODUCING SAME

[75] Inventors: Kazuo Ohtsuki; Akikazu Mitsunobu; Yoshihiro Imaizumi, all of Tokyo; Nobuyoshi Honda; Satoshi Inoue, both of Ishibashi, all of Japan

[73] Assignees: Nippon Kayaku Kabushiki Kaisha, Tokyo; Snow Brank Milk Products Co., Ltd., Sapporo, both of Japan

[21] Appl. No.: 453,875

[22] Filed: May 30, 1995

Related U.S. Application Data

[62] Division of Ser. No. 247,778, May 23, 1994.

[30] Foreign Application Priority Data

May 28, 1993 [JP] Japan ................. 5-151320

[51] Int. Cl.⁶ ....................... C07J 1/00; C07J 75/00
[52] U.S. Cl. ........................................... 552/615
[58] Field of Search ............................. 552/615

[56] References Cited

U.S. PATENT DOCUMENTS

| | | | |
|---|---|---|---|
| 4,975,368 | 12/1990 | Yoshihama et al. | 435/60 |
| 5,098,535 | 3/1992 | Nakakoshi et al. | 552/615 |

FOREIGN PATENT DOCUMENTS

| | | |
|---|---|---|
| 0300062 | 1/1989 | European Pat. Off. |
| 0382162 | 8/1990 | European Pat. Off. |

OTHER PUBLICATIONS

Remington's Pharmaceutical Sciences, 15th Edition, 1975, p. 1358.
Shibata, Megumi, et al. "X-ray Structural Studies and Physicochemical Properties of Cimetidine Polymorphism", Journal of Pharmaceutical Sciences, vol. 72, No. 12, Dec. 1983; pp. 1436–1442.
Remington's Pharmaceutical Sciences, 18th Edition, 1990, pp. 1439–1443.
Ashizawa, Kazuhide, et al., "Pseudopolymorphism and Phase Stability in Four Solid Forms of (6R,7R-7-[2-(5-Amino-1,2,4-thiadiazol-3-yl)-(Z)-2-methoxy-iminoacetamid]-3-[(4-carbamoyl-1-quinuclidinio)methyl]-8-oxo-5-thia-1-azabicyclo-[4,2,0]oct-2-ene-2-carboxylate (E1040)," Journal of Pharmaceutical Sciences, vol. 78, No. 11, Nov. 1989, pp. 893–899.
Patent Abstracts of Japan vol. 017, No. 394 (C–1088), 23 Jul. 1993 & JP-A-05076387 (Snow Brand Milk Prod Co Ltd), 30 Mar. 1993 *Abstract* & Database WPI Section Ch, Week 9317 Derwent Publications Ltd., London, GB; Class B01, An 93–139581.
Patent Abstracts of Japan vol. 015, No. 227 (C–0839), 10 Jun. 1991 & JP-A-03068596 (Snow Brand Milk Prod Co Ltd), 25 Mar. 1991, *Abstract* & Database WPI Section Ch Week 9118 Derwent Publications Ltd., London, GB; Class B01, AN 91–129147.
Chemical Abstracts, vol. 111, No. 1, 3 Jul. 1989, Columbus, Ohio, US; abstract No. 3930, M. Yoshihama et al: "Microbial Production of two new dihydroxylated androstenedione deriatives by Acremonium strictum" p. 380; column 2; XP002001152 *Abstract & J. Ferment. BioEng., vol. 67, No. 4, 1989, pp. 238–243.
P.D. Kennewell: "Comprehensive Medicinal Chemistry (The Rational Design, Mechanistic Study & Therapeutic Application of Chemical Compounds)" 1990, Permagon Press, Oxford, G.B. XP002001151 *p. 356–p. 359* *in particular, p. 356, paragraph 3.6.4.5.2*.

Primary Examiner—Kimberly J. Prior
Attorney, Agent, or Firm—Nields & Lemack

[57] ABSTRACT

Provided are stable hydrate crystals of 14α-hydroxy-4-androstene-3,6,17-trione having a biological activity of human placenta-originating estrodiene synthesis enzyme inhibitory action. These hydrate crystals include two kinds of 14α-hydroxy-4-androstene-3,6,17-trione hydrate crystals having a diffraction pattern having characteristic peaks at diffraction angles in crystalline powder X-ray diffraction. Processes for producing these hydrate crystals are also provided.

2 Claims, 9 Drawing Sheets

α – TYPE CRYSTAL

β-TYPE CRYSTAL

α – TYPE CRYSTAL

β - TYPE CRYSTAL

Y-TYPE CRYSTAL

14α-HYDROXY-4-ANDROSTENE-3,6,17-TRIONE HYDRATE AND PROCESS FOR PRODUCING SAME

This application is a divisional of application Ser. No. 08/247,778 filed May 23, 1994 (pending).

BACKGROUND OF THE INVENTION

The present invention relates to 14α-hydroxy-4-androstene-3,6,17-trione hydrate crystals and a process for producing the same.

14α-hydroxy-4-androstene-3,6,17-trione has a biological activity of human placenta-originating estrodiene synthesis enzyme inhibiting action and development thereof as an anticancer medicine has been expected.

14α-hydroxy-4-androstene-3,6,17-trione is a known compound and can be synthesized, for example, by the process disclosed in Japanese Patent Kokoku No. 1-32236 (EP-A 300062). According to this process, 6β,14α-dihydroxy-4-androstene-3,17-dione is dissolved in chloroform and an oxidizing agent is added to the solution to carry out the reaction. After completion of the reaction, the reaction mixture is filtrated to remove the oxidizing agent and the residue is sufficiently washed. Then, the solvent is removed to obtain a crude fraction. This fraction is dissolved in a small amount of chloroform or methanol and the solution is subjected to high performance liquid chromatography (HPLC) to elute and isolate 14α-hydroxy-4-androstene-3,6,17-trione.

The 14α-hydroxy-4-androstene-3,6,17-trione is obtained as a crystal by distilling off the solvent from the organic solvent solution. The above patent publication mentions that thus obtained crystal is white, but strictly speaking this is yellow.

The 14α-hydroxy-4-androstene-3,6,17-trione which is first obtained in the form of an organic solvent solution and finally obtained by distilling off the solvent from the organic solvent solution is an anhydride crystal which has hygroscopicity and which changes its color upon absorption of water. Therefore, the compound is difficult to handle in the formulation step and is not suitable as preparations for medicines.

That is, the 14α-hydroxy-4-androstene-3,6,17-trione anhydride crystal (hereinafter referred to as "α-type crystal") readily absorbs water during storage or formulation and increases in its weight and changes to slightly yellowish white in its color. Therefore, when the α-type crystal is used, there occur errors in weighing, unevenness in the color of medicines prepared therefrom and differences in the color of respective lots of preparations. Thus, it is difficult to obtain medicines of uniform quality. Accordingly, the object of the present invention is to provide 14α-hydroxy-4-androstene-3,6,17-trione suitable as starting preparations for medicines.

SUMMARY OF THE INVENTION

As a result of intensive research conducted by the inventors, it has been found that 14α-hydroxy-4-androstene-3,6,17-trione has polymorphism in its crystal form, namely, in addition to the anhydride crystal there exist two kinds of stable hydrate crystals free from the problems of hygroscopicity and change in color, and the present invention has been accomplished. That is, the present invention provides 14α-hydroxy-4-androstene-3,6,17-trione hydrate crystals and a process for producing same. The detail of the present invention are as follows.

According to the present invention there is provided 14α-hydroxy-4-androstene-3,6,17-trione hydrate crystal which is characterized by having a diffraction pattern where characteristic peaks in crystalline powder X-ray diffraction of characteristic X-ray Cu Kα appear at diffraction angles of 10.7, 14.2, 14.8, 15.7, 16.3 and 17.8 (degree) (hereinafter referred to as "β-type crystal").

Further, according to the present invention, there is provided 14α-hydroxy-4-androstene-3,6,17-trione hydrate crystal which is characterized by having a diffraction pattern where characteristic peaks in crystalline powder X-ray diffraction of characteristic X-ray Cu Kα appear at diffraction angles of 7.9, 10.7, 14.2, 15.9, and 18.5 (degree) (hereinafter referred to as "γ-type crystal").

Furthermore, according to the present invention, there is provided a process for producing the β-type crystal which is characterized by suspending the α-type crystal or the γ-type crystal in water. Moreover, according to the present invention, there is provided a process for producing the γ-type crystal which is characterized by carrying out crystallization from an organic solvent solution of 14α-hydroxy-4-androstene-3,6,17-trione in the presence of water.

DETAILED DESCRIPTION OF THE INVENTION

Figure 1:
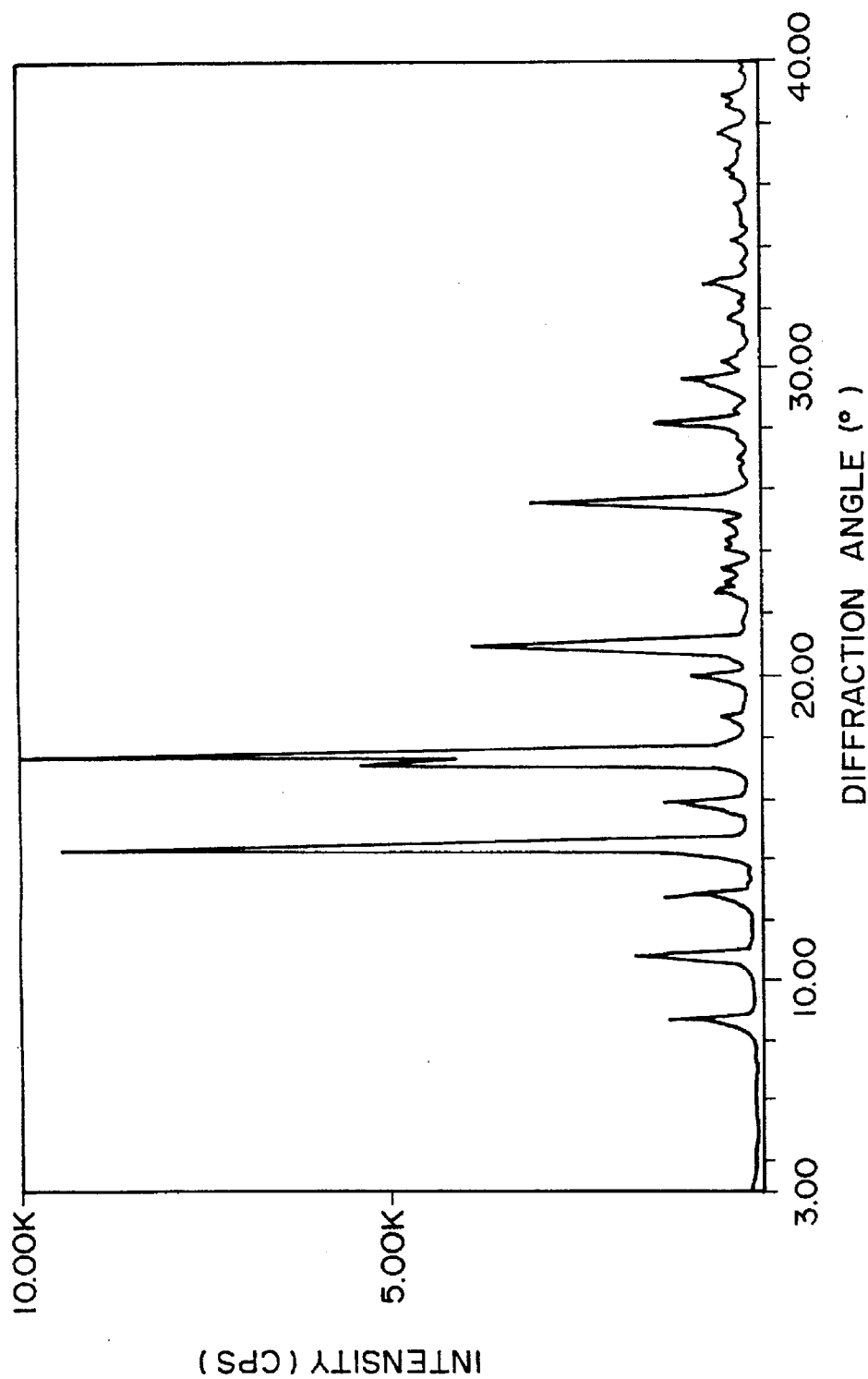
FIG. 1 shows the crystalline powder X-ray diffraction pattern of 14α-hydroxy-4-androstene-3,6,17-trione anhydride crystal (α-type crystal).
Figure 2:
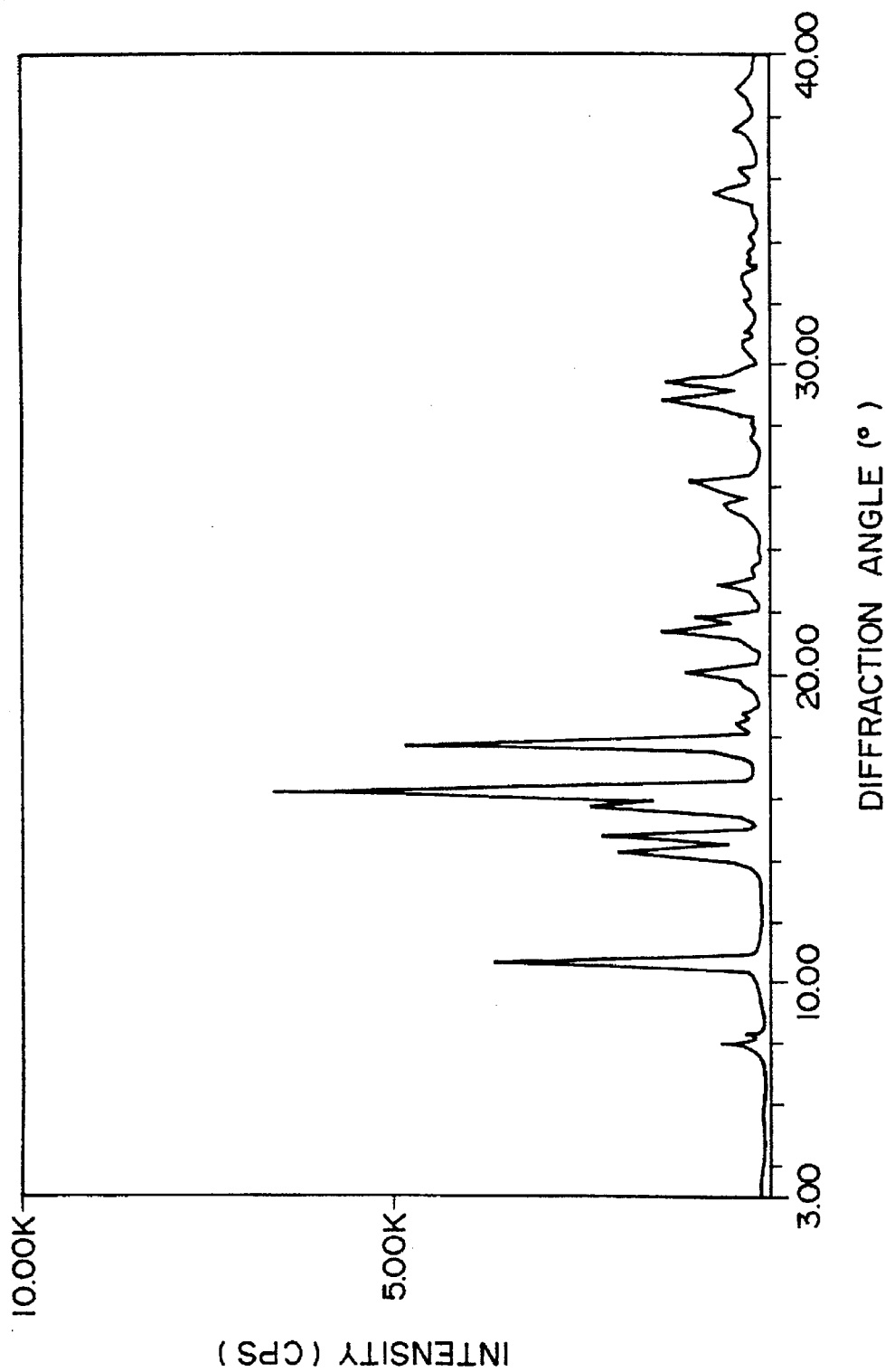
FIG. 2 shows the crystalline powder X-ray diffraction pattern of 14α-hydroxy-4-androstene-3,6,17-trione hydrate crystal (β-type crystal).
Figure 3:
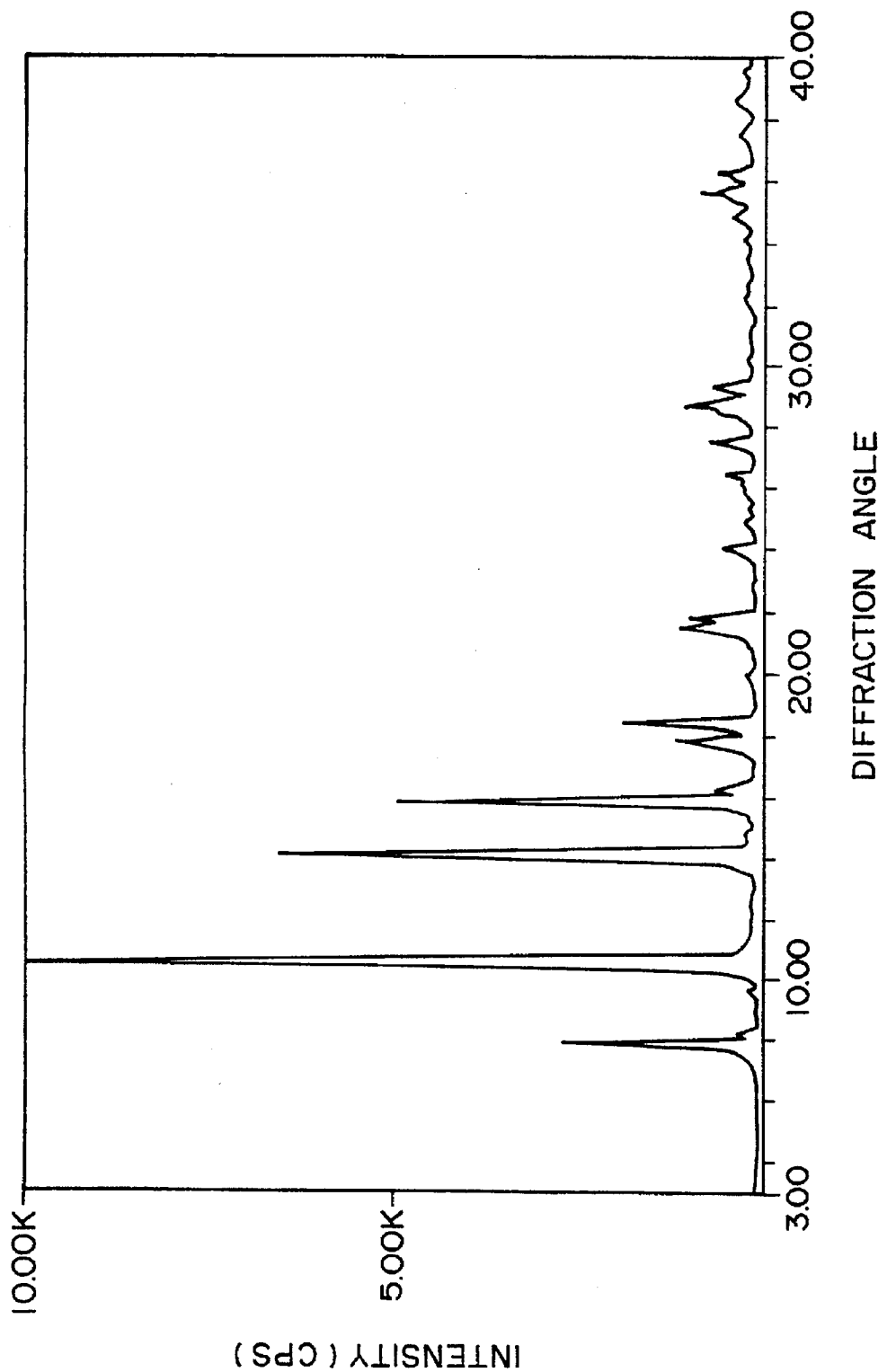
FIG. 3 shows the crystalline powder X-ray diffraction pattern of 14α-hydroxy-4-androstene-3,6,17-trione hydrate crystal (γ-type crystal).
Figure 4:
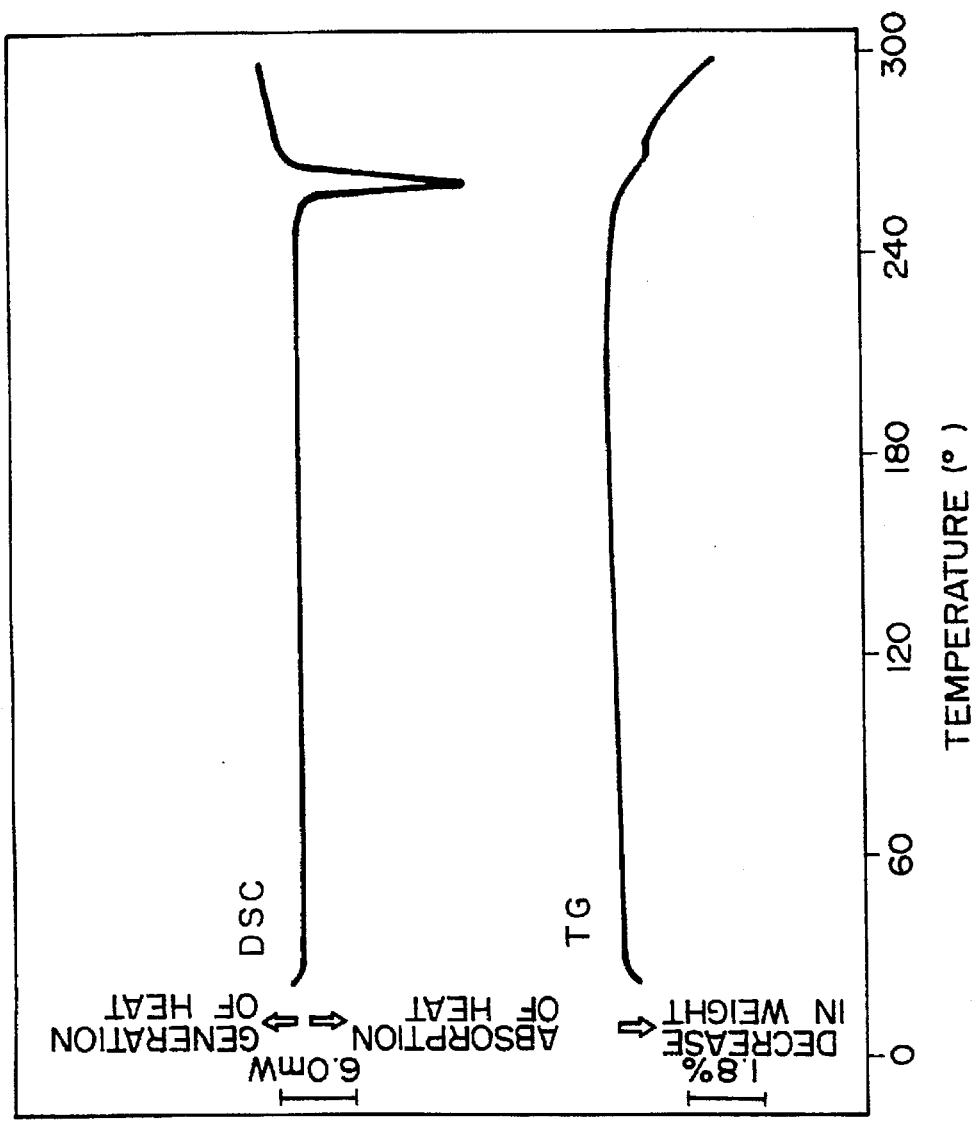
FIG. 4 shows the charts of thermal analyses (DSC (differential scanning calorimetry) and TG (thermogravimetic analysis)) of the α-type crystal.
Figure 5:
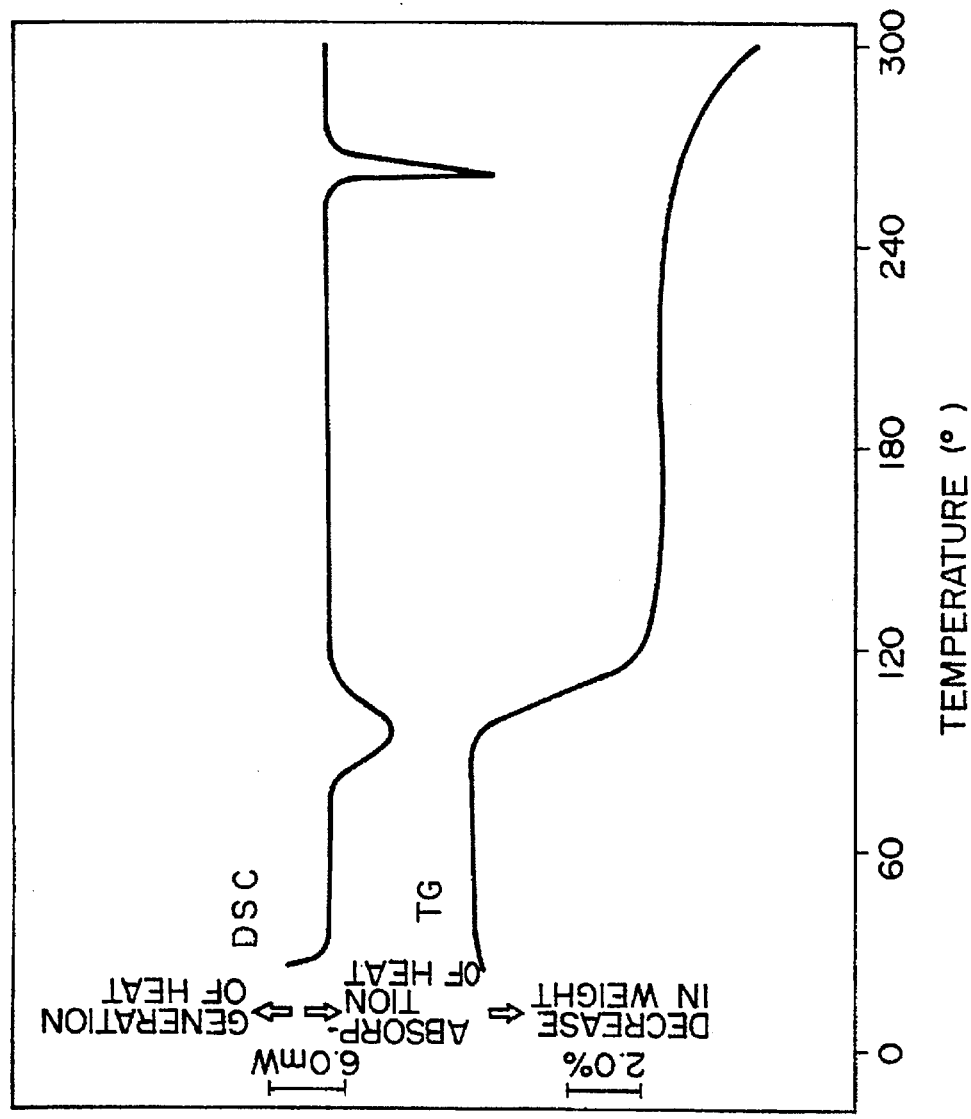
FIG. 5 shows the charts of the thermal analyses of the β-type crystal.
Figure 6:
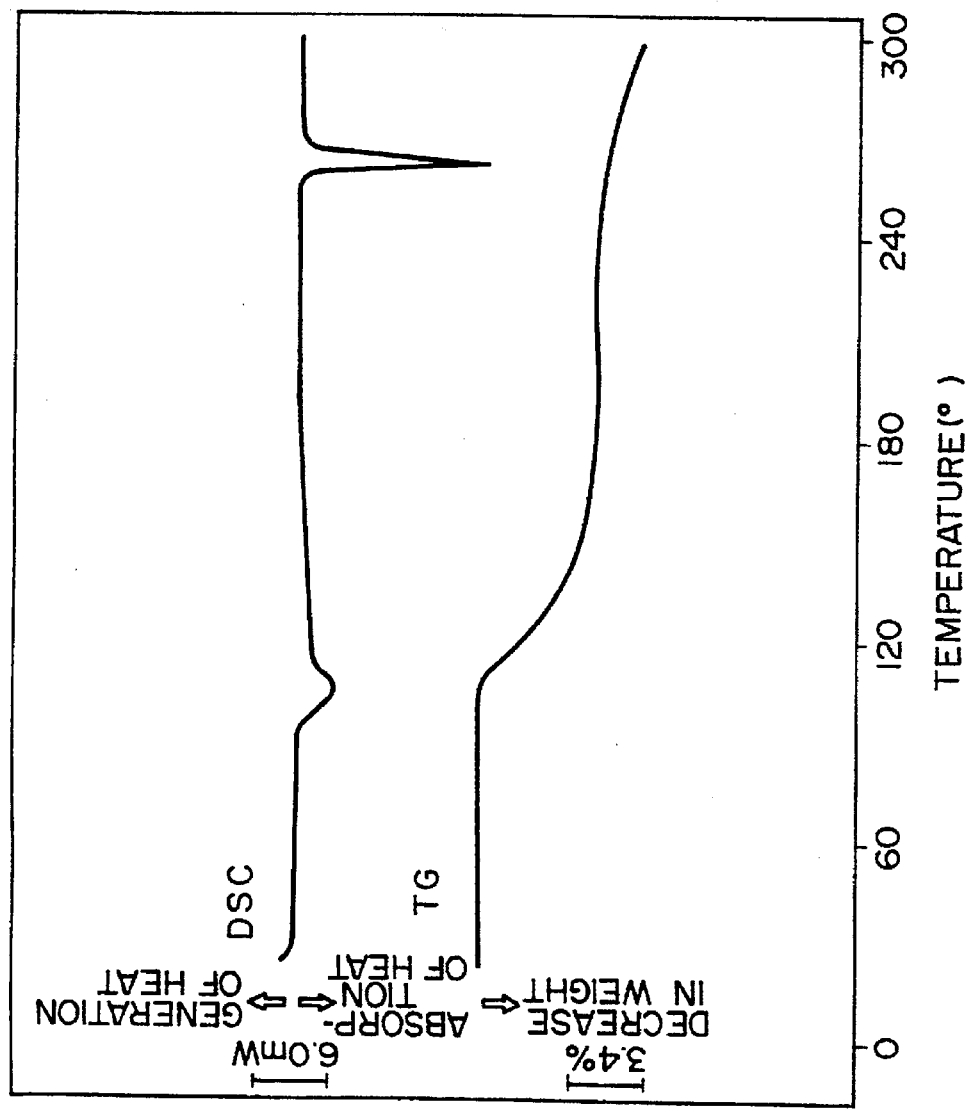
FIG. 6 shows the charts of the thermal analyses of the γ-type crystal.
Figure 7:
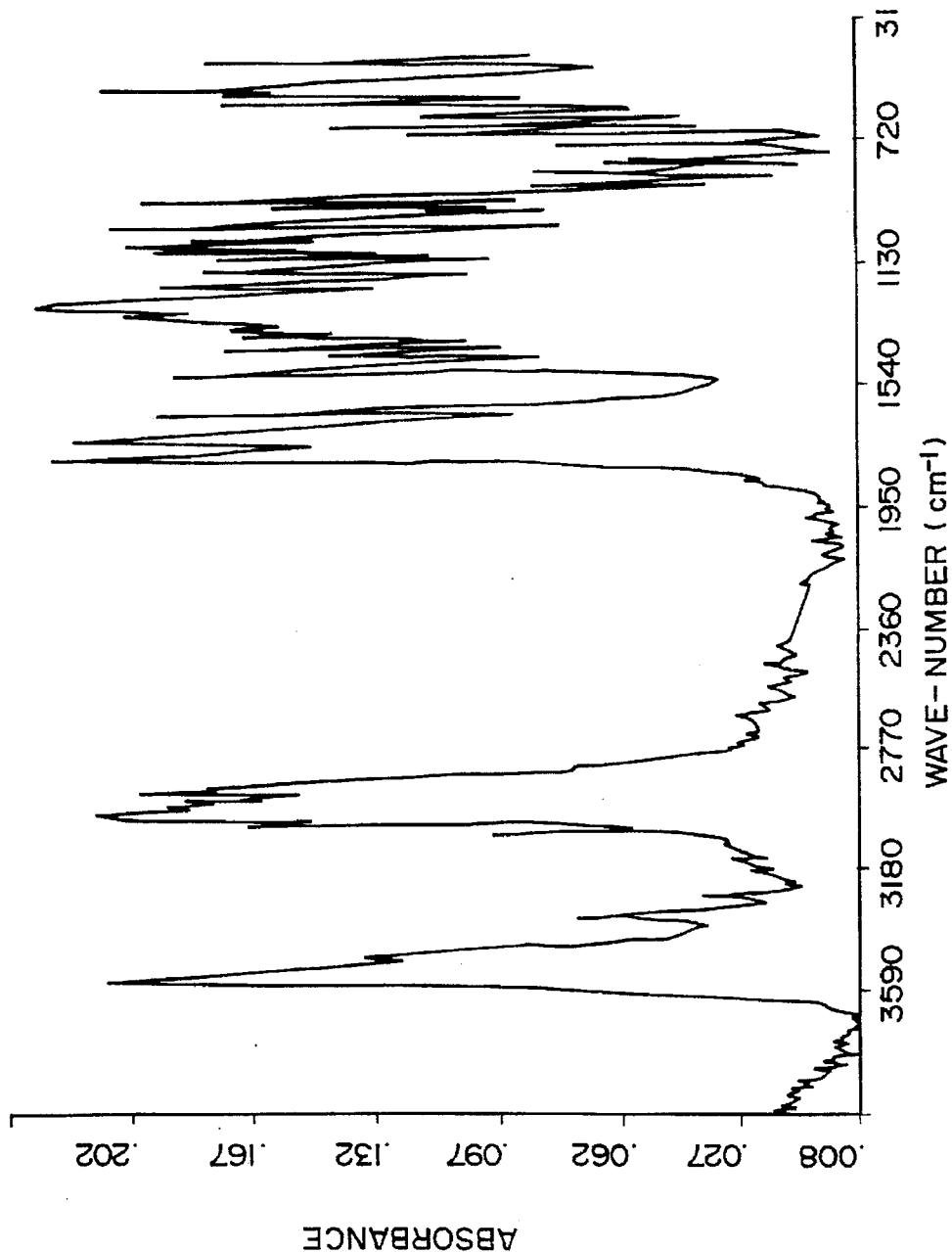
FIG. 7 shows the FT-IR spectrum (Fourier transformation-infrared spectrum) of the α-type crystal.
Figure 8:
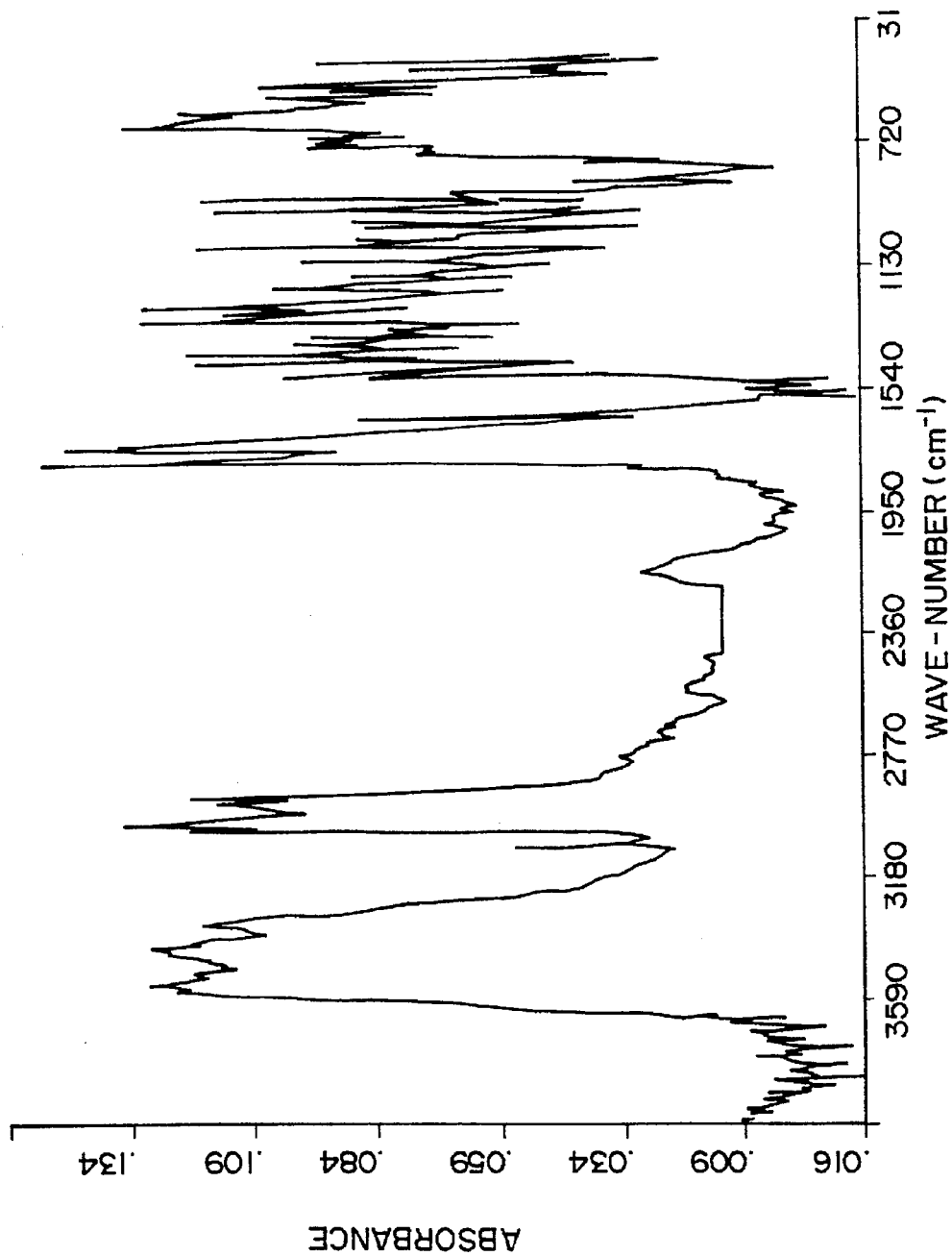
FIG. 8 shows the FT-IR spectrum of the β-type crystal.
Figure 9:
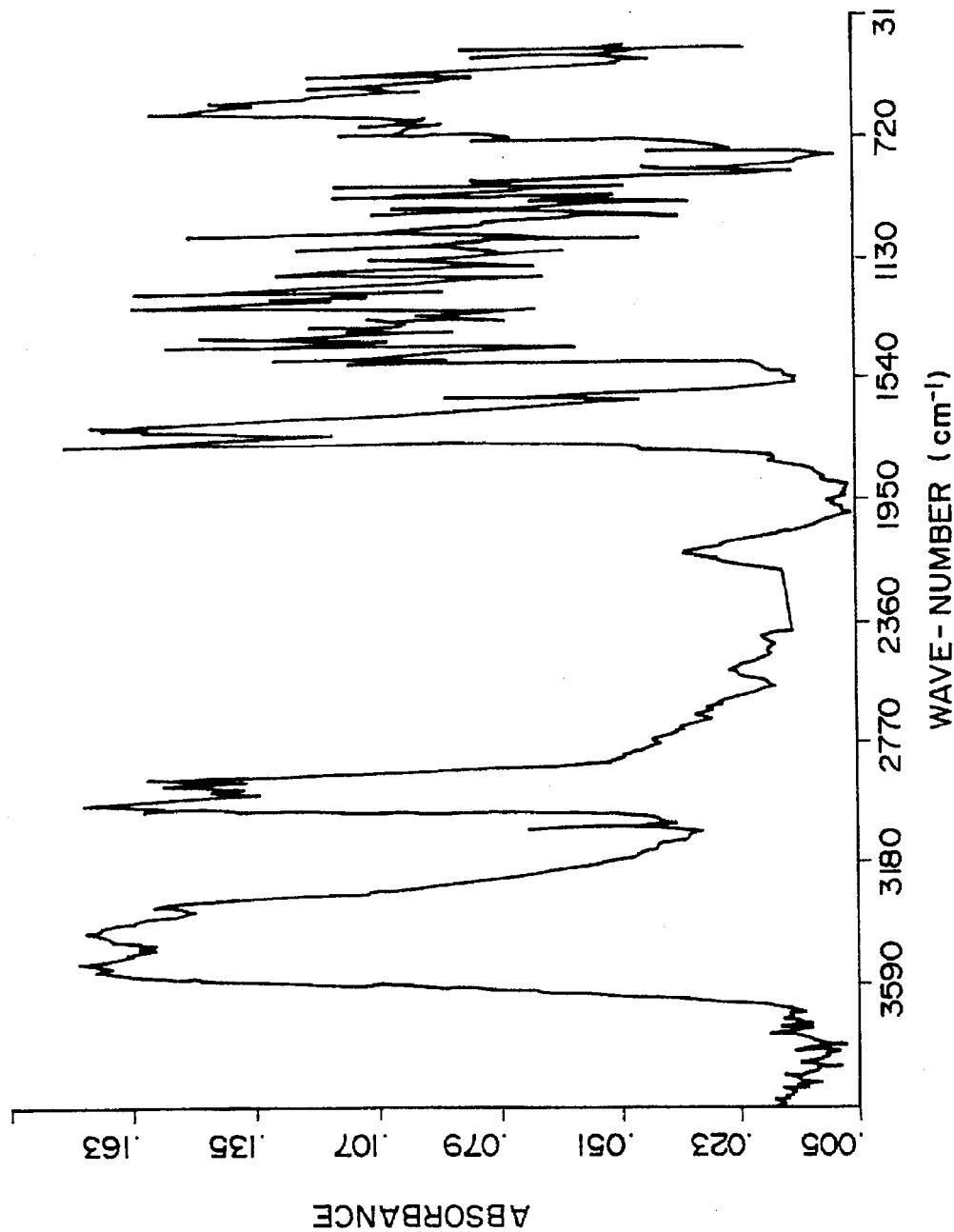
FIG. 9 shows the FT-IR spectrum of the γ-type crystal.

The hydrate crystal of the present invention is produced using the α-type crystal as a starting material. The α-type crystal can be obtained by the process described in the patent publication cited hereabove.

That is, a specific microorganism for example FERM P-9143 (deposited on Jan. 21, 1987 in Fermentation Research Institute, Agency of Industrial Science and Technology, 1–3, Higashi 1-chome, Tsukuba-shi, Ibaraki-ken, 305, Japan, and then transferred to FERM BP-2716 under the Budapest Treaty on Dec. 27, 1989 in said depository) belonging to the genus, Acremonium is allowed to act on 4-androstene-3,17-dione as a substrate to produce 6β,14α-dihydroxy-4-androstene-3,17-dione. Furthermore, this 6β,14α-dihydroxy-4-androstene-3,17-dione is allowed to react in the presence of an oxidizing catalyst to obtain a crude fraction of 14α-hydroxy-4-androstene-3,6,17-trione.

Then, the fraction is dissolved in a small amount of chloroform or methanol. The solution is subjected to HPLC using a silica gel column and an elution solvent (chloroform: methanol=98:2) to elute and isolate 14α-hydroxy-4-androstene-3,6,17-trione. The solvent was removed from the isolated solution to obtain the α-type crystal of 14α-hydroxy-4-androstene-3,6,17-trione. This α-type crystal has such a diffraction pattern where characteristic peaks in crystalline powder X-ray diffraction of characteristic X-ray Cu Kα appear at diffraction angles of 12.7, 14.5, 17.3, 17.6, 21.1 and 25.7 (degree).

The β-type crystal of the present invention can be produced by suspending in water the α-type crystal or the γ-type crystal which is produced, for example, from the α-type crystal by the process mentioned hereinafter. The suspending treatment is preferably carried out under stirring at 0° C. to 100° C. and, usually, room temperature suffices as the suspending temperature. Amount of water is not critical and may be such amount as capable of sufficiently immersing the α-type crystal or the γ-type crystal. Usually, the amount is 1–10 times (V/W) the weight of the crystal. The suspending time may be short and the termination is determined by crystalline powder X-ray diffraction, and at least one hour, preferably at least 2 hours is sufficient.

The β-type crystal of the present invention can also be produced by moistening the α-type crystal until it reaches moisture equilibrium. The moistening treatment is preferably carried out under the conditions of a temperature of 10° C. or higher and a relative humidity of 75% or higher, preferably 40°–80° C. and 75–100%. Specifically, this is carried out by storing the α-type crystal in a desiccator containing a saturated aqueous solution of an inorganic salt such as potassium nitrate until it reaches the moisture equilibrium with no increase in weight.

The β-type crystal of the present invention has such a diffraction pattern where characteristic peaks in crystalline powder X-ray diffraction of characteristic X-ray Cu Kα appear at diffraction angles of 10.7, 14.2, 14.8, 15.7, 16.3 and 17.8 (degree). This β-type crystal is a slightly yellowish white powder and is a monohydrate according to the results of measurement of water content with Karl Fischer's reagent and the results of TG.

The γ-type crystal of the present invention can be obtained by crystallization from an organic solvent solution of 14α-hydroxy-4-androstene-3,6,17-trione in the presence of water. The organic solvent solution can be obtained by isolating a fraction containing 14α-hydroxy-4-androstene-3,6,17-trione from the reaction mixture for synthesis of the compound by liquid chromatography or by dissolving the known α-type crystal in an organic solvent or a water-containing organic solvent containing water in such an amount as not adversely affecting the solubility of the compound.

The process of crystallization from an organic solvent solution in the presence of water is carried out by lowering the solubility of 14α-hydroxy-4-androstene-3,6,17-trione, for example, by increasing the proportion of water in the organic solvent solution with addition of water or by cooling the organic solvent solution. As the organic solvent, there may be used polar organic solvents such as methanol, ethanol, acetone, dioxane, dimethyl sulfoxide, and dimethylformamide. The amount of water can be optionally determined considering the solubility of 14α-hydroxy-4-androstene-3,6,17-trione in the organic solvent. It is preferable to allow the presence of water in an amount equimolar or more with the compounds dissolved in the organic solvent. The amount of water is usually 2% (v/v) or more, preferably 3% (v/v) or more, more preferably 4% (v/v) or more based on a total amount of the water and the organic solvent.

The γ-type crystal of the present invention has such a diffraction pattern where characteristic peaks in crystalline powder X-ray diffraction of characteristic X-ray Cu Kα appear at diffraction angles of 7.9, 10.7, 14.2, 15.9, and 18.5 (degree). Like the β-type crystal, this γ-type crystal is a slightly yellowish white powder and is a monohydrate according to the results of measurement of water content with Karl Fischer's reagent and the results of TG.

The β-type crystal and the γ-type crystal of the present invention both have the features that as is clear from the results of stability tests conducted in the following examples, they have no hygroscopicity and crystal water does not devolatilize even when they are vacuum dried in a desiccator in the presence of diphosphorus pentoxide, and furthermore they are stable against heat and light and do not change in the color. Accordingly, errors in weighing and occurrence of uneven color of preparations and difference in color of respective lots can be prevented in the step of formulation, and medicines of uniform quality can be easily obtained. Therefore, they are excellent as starting preparations for medicines. Incidentally, there occurs in some cases a little slippage of the characteristic peaks of crystalline powder X-ray diffraction of β-type and γ-type crystals depending on the apparatus and measuring methods. However, the crystals showing the essentially same peaks are involed in the present invention.

Since the γ-type crystal transforms to the β-type crystal upon being suspended in water or under the mechanochemical conditions such as grinding and compression, it is preferred to use the β-type crystal which is the most stable in the crystal form when uniform crystal form is required in preparation of medicines.

The present invention is explained in detail by the following examples, but these examples should not be construed as limiting the invention in any manner.

EXAMPLE 1

5 g of the α-type crystal (water content: 1.9%) and 10 ml of distilled water were charged in a 30 ml egg-plant type flask and stirred for 2 hours in the suspended state. Then, crystal was recovered from the suspension by suction filtration and the recovered crystal was vacuum dried overnight in the presence of diphosphorus pentoxide to obtain 5.1 g of slightly yellowish white β-type crystal (water content: 5.4%). Identification of the β-type crystal was conducted by crystalline powder X-ray diffractometry (Cu Kα), thermal analysis and Fourier transformation-infrared spectrum (FT-IR, measuring method: diffused reflectance spectroscopy of powder sample). The water content was measured by Karl Fischer's moisture meter. The results of stability test for the above β-type crystal are shown in Tables 1 and 2.

EXAMPLE 2

0.501 g of the α-type crystal (water content: 1.0%) was taken in a weighing bottle and was stored in a desiccator containing a saturated aqueous potassium nitrate solution for 4 days at 40° C. to obtain 0.526 g of slightly yellowish white β-type crystal. Identification of the β-type crystal was conducted in the same manner as in Example 1.

EXAMPLE 3

10 g of the α-type crystal (water content: 1.9%) was taken in a filter paper thimble and refluxed under heating with 300 ml of distilled water-acetone (5:95) and continuously extracted by Soxhlet's extractor. After cooling, the crystal precipitated in the flask part was recovered by suction filtration and the recovered crystal was vacuum dried overnight in the presence of diphosphorus pentoxide to obtain 9.7 g of slightly yellowish white γ-type crystal (water content: 5.4%). Identification of the γ-type crystal and measurement of water content were conducted in the same manner as in Example 1. The results of stability test for the above γ-type crystal are shown in Tables 1 and 2.

EXAMPLE 4

1 g of the α-type crystal (water content: 1.9%) was taken in a 200 ml egg-plant type flask and 54 ml of methanol was added thereto and the crystal was dissolved with heating. Thereto was added 6 ml of distilled water, followed by refluxing under heating and then cooling with ice. The precipitated crystal was recovered by suction filtration and the recovered crystal was vacuum dried overnight in the presence of diphosphorus pentoxide to obtain 0.8 g of slightly yellowish white γ-type crystal. Identification of the γ-type crystal and measurement of water content were conducted in the same manner as in Example 1.

TABLE 1

Appearance of crystal and change of water content
(Test was conducted by storing the crystal in an
atmosphere of 40° C. and 75% RH.)

| After form | Storage day | | | |
|---|---|---|---|---|
| | 0 day | 3 days | 7 days | 14 days |
| <α-type crystal> | | | | |
| Appearance | Yellow | Slightly yellowish white | Slightly yellowish white | Slightly yellowish white |
| Water content (wt. %) | 1.0 | 3.2 | 3.9 | 4.4 |
| <β-type crystal> | | | | |
| Appearance | Slightly yellowish white | No change | No change | No change |
| Water content (wt. %) | 5.5 | 5.5 | 5.4 | 5.5 |
| <γ-type crystal> | | | | |
| Appearance | Slightly yellowish white | No change | No change | No change |
| Water content (wt. %) | 5.6 | 5.4 | 5.4 | 5.4 |

(Note) The water content in the sample at a storage day of 0 was measured by Karl Fischer's moisture meter and the water content of the samples thereafter was calculated from the rate of change in weight.

TABLE 2

Stability of hydrate crystal

| Storage conditions | Crystal form | | | |
|---|---|---|---|---|
| | β-type crystal | | γ-type crystal | |
| | Appearance | Purity | Appearance | Purity |
| Initial | Slightly yellowish white | 99.2% | Slightly yellowish white | 99.6% |
| 65° C./8 weeks | No change | 99.1% | No change | 99.4% |
| 40° C./3 months | No change | 98.6% | No change | 99.5% |
| White fluorescent lamp/ 1,200,000 L × hr | No change | 99.6% | No change | 100.0% |
| Chemical lamp/ 7 days | No change | 99.3% | No change | 100.0% |

(Note) The purity was measured by HPLC.

Using the β-type crystal and the γ-type crystal of the present invention, medicines of a uniform content and a uniform color can be easily obtained because they undergo no change due to temperature, humidity and light during the period of from preparation of medicines to circulation thereof as described hereabove.

What is claimed is:

1. A process for producing 14α-hydroxy-4-androstene-3,6,17-trione hydrate crystal having a diffraction pattern where characteristic peaks in crystalline powder X-ray diffraction of characteristic X-ray Cu Kα appear at diffraction angles of 10.7, 14.2, 14.8, 15.7, 16.3 and 17.8 (degree), which comprises suspending in water an anhydride crystal of 14α-hydroxy-4-androstene-3,16,17-trione or 14α-hydroxy-4-androstene-3,6,17-trione hydrate crystal having a diffraction pattern where characteristic peaks in crystalline powder X-ray diffraction of characteristic X-ray Cu Kα appear at diffraction angles of 7.9, 10.7, 14.2, 15.9, and 18.5 (degree).

2. A process for producing 14α-hydroxy-4-androstene-3,6,17-trione hydrate crystal having a diffraction pattern where characteristic peaks in crystalline powder X-ray diffraction of characteristic X-ray Cu Kα appear at diffraction angles of 7.9, 10.7, 14.2, 15.9, and 18.5 (degree), which comprises carrying out crystallization from an organic solvent solution of 14α-hydroxy-4-androstene-3,6,17-trione in the presence of at least 2% (v/v) water.

* * * * *